United States Patent [19]
Austin, Jr. et al.

[11] Patent Number: 5,332,194
[45] Date of Patent: Jul. 26, 1994

[54] FLUID FLOW CONTROLLER

[75] Inventors: George K. Austin, Jr., Newberg; Sandor Johannes, West Linn; Theodore E. Schmidt, Carlton, all of Oreg.

[73] Assignee: A-Dec, Inc., Newberg, Oreg.

[21] Appl. No.: 13,310

[22] Filed: Feb. 4, 1993

[51] Int. Cl.⁵ ............................................. F16K 31/00
[52] U.S. Cl. ................................... 251/345; 251/344
[58] Field of Search ......................... 251/343, 344, 345

[56] References Cited
U.S. PATENT DOCUMENTS

| | | | |
|---|---|---|---|
| 453,109 | 5/1891 | Dreisorner | 251/345 |
| 2,590,368 | 3/1952 | Beck | 251/344 |
| 3,788,603 | 1/1974 | Snider | 251/345 |
| 4,603,837 | 8/1986 | Steer | 251/345 |

Primary Examiner—A. Michael Chambers
Attorney, Agent, or Firm—Klarquist, Sparkman, Campbell, Leigh & Whinston

[57] ABSTRACT

A valve assembly for controlling fluid flow to a tube connected to the assembly by shifting of a sleeve mounted on the assembly. When the sleeve is shifted into a shutoff position, a fluid path through the assembly is completely occluded by a closure element in the sleeve. As the sleeve is rotated away from its shutoff position, the fluid path is gradually opened.

16 Claims, 4 Drawing Sheets

FLUID FLOW CONTROLLER

The present invention relates to a valve assembly for use with fluid-carrying conduits, and more particularly to such an assembly for selectively controlling the rate of fluid flow through the conduits.

BACKGROUND AND SUMMARY OF THE INVENTION

Tubes for carrying fluid are used in many applications in the health care industry. For example, most dental offices use water supplied to various dental appliances for rinsing and cleaning the patient's teeth during dental procedures. In general, water is supplied to the appliances through a panel-mounted connector which is plumbed to a source of water. The appliance generally has only a simple on-off control for opening and closing a valve located on the appliance. The rate of flow typically is controlled by means of a standard stemmed flow control valve attached somewhere in the fluid line, generally near the panel.

Such standard flow control valves generally are bulky and may be inconvenient to adjust. They also may be difficult to clean and sanitize.

The present invention is directed to a valve assembly for use with fluid flow conduits, or tubes. The rate of fluid flow through a tube attached to the valve assembly is controlled by shifting of a sleeve which is mounted on the assembly. When the sleeve is shifted to a shutoff position, all flow of fluid through the valve assembly is stopped. Shifting of the sleeve away from the shutoff position opens a fluid path through the valve, thereby permitting fluid to flow to downstream apparatus. The rate of fluid flow is increased or decreased by incremental shifting of the sleeve in the assembly. The sleeve is configured so that precise adjustment of the rate of fluid flow is possible.

A general object of the present invention is to provide a novel fluid flow control valve which is simple and inexpensive to construct, yet which provides smooth variation in fluid flow rates between full-off and full-on positions.

Another object of the invention is to provide such a novel fluid flow control valve which when operated in one direction produces gradual variation in fluid flow rate and when operated in another direction produces rapid variations in fluid flow rates.

The flow control assembly of one embodiment of the present invention utilizes a rotatable sleeve with a helical closure element formed on an inner wall of the sleeve. The sleeve is mounted over a body which is connected to a fluid source, and which includes fluid passageways for carrying fluid. When the sleeve is rotated into the shutoff position, the fluid passageway through the valve is completely occluded to prevent fluid flow through the valve assembly. As the sleeve is rotated away from its shutoff position the fluid path is opened gradually so that the rate of fluid flow increases as the valve is rotated.

In another embodiment of the invention a sleeve is mounted for shifting longitudinally along a valve body which includes fluid passages. The sleeve is threadedly connected to the body and has a valve closure element therein which is positioned to close the fluid passage when in its shutoff position and to allow fluid flow when in its open position. Rotation of the sleeve about the body causes the sleeve and closure element to shift gradually between the open and shutoff positions.

A dental appliance having a simple on-off valve may be attached to the present flow control assembly with a standard quick connect device.

The device allows the user to adjust the rate of fluid flow in a precise manner. In addition, the device is convenient to use, small, and easily cleaned and sanitized. Moreover, the valve assembly of the present invention may be utilized with any fluid, such as water or air.

DETAILED DESCRIPTION OF PREFERRED EMBODIMENTS

Figure 1:
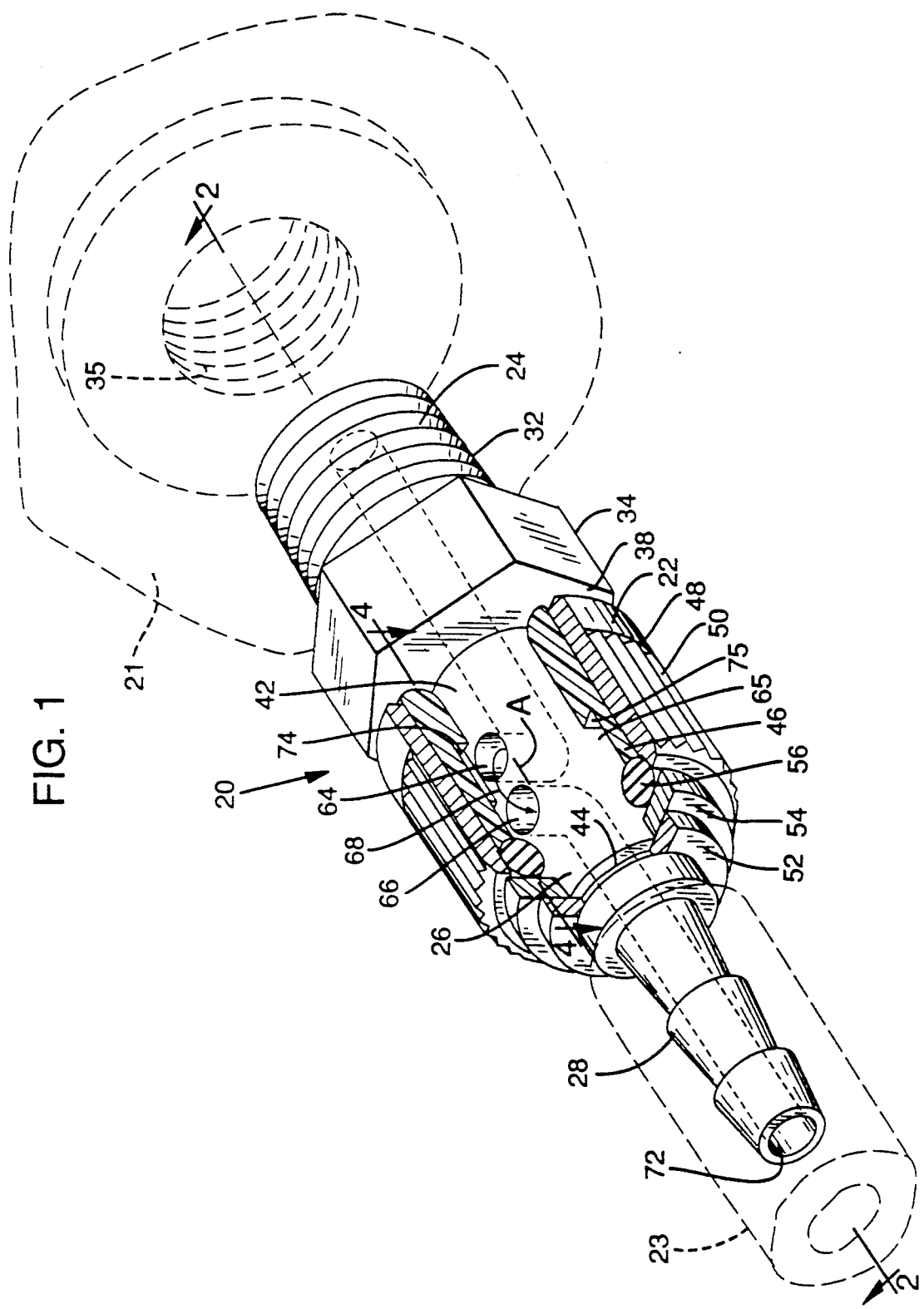
FIG. 1 is a perspective view of the valve assembly according to an embodiment of the present invention with portions broken away to illustrate internal structure.
Figure 2:
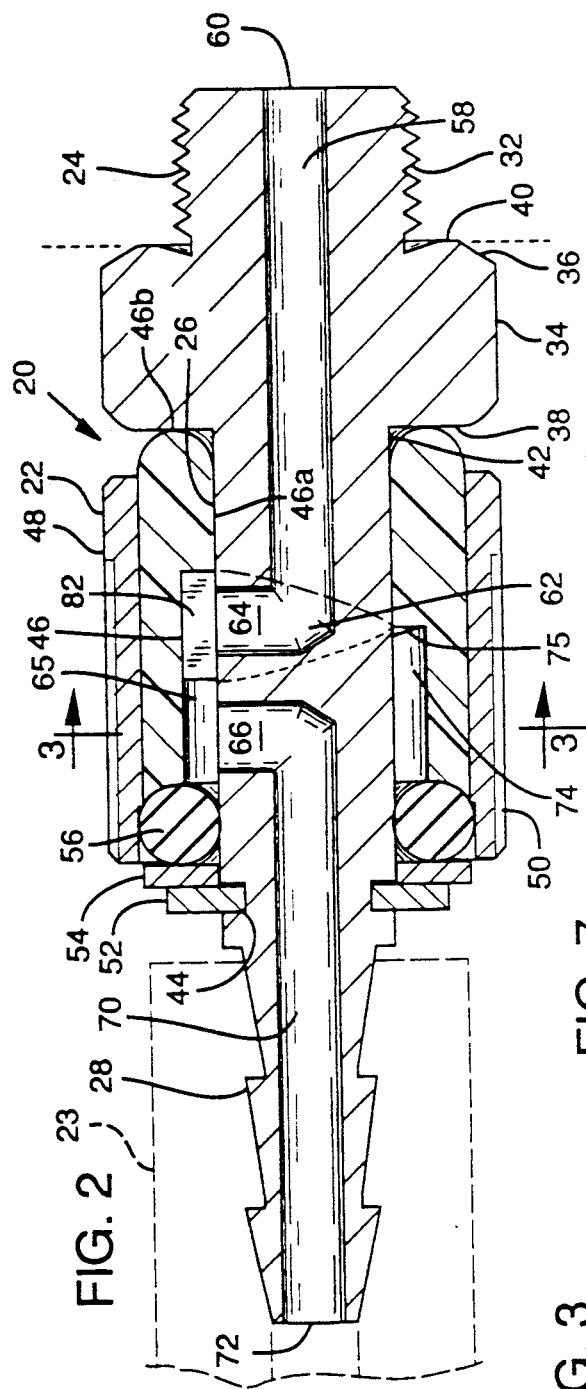
FIG. 2 is a sectional view taken along line 2—2 of FIG. 1.
Figure 3:
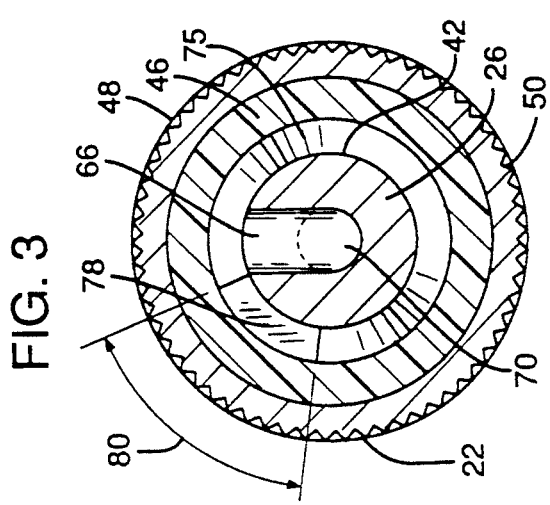
FIG. 3 is a cross-sectional view taken along line 3—3 of FIG. 2.

With reference to FIGS. 1-2, a valve assembly 20 according to an embodiment of the present invention is illustrated used for controlling fluid flow from a fluid source in a panel, shown in dotted outline at 21, to a downstream tube, shown in dotted outline at 23. The tube may be connected to an appliance, such as a dentist's syringe, to provide fluid thereto.

The flow of fluids, such as water or air, is controlled by rotation of a cylindrical flow control sleeve 22, also referred to herein as a housing. When sleeve 22 is rotated into a shutoff position, all flow of fluid through valve assembly 20 is stopped. Rotation of sleeve 22 away from the shutoff position opens a fluid path through the valve, thereby permitting fluid to flow to downstream apparatus. The valve assembly has been found to have significant benefits for medical-dental fluid flow appliance use.

Valve assembly 20 comprises an elongate, generally cylindrical body 26. A cylindrical threaded portion 24 extends from one end thereof. An elongate cylindrical barbed tube connector nozzle 28 extends from the opposite end of body 26.

Threaded portion 24 has external threads 32 and a hexagonal head portion 34. It can be screwed into a threaded socket 35 in panel 21 to provide a fluid-tight connection between the valve assembly and a fluid source in panel 21.

Body portion 26 has a smooth cylindrical external surface, or sidewall, 42. An annular groove 44 is defined between nozzle 28 and cylindrical surface 42. Cylindrical sleeve 22 is sealingly mounted on surface 42 of body 26 for rotation thereabout.

An internal inflow conduit, or fluid flow passageway, 58 extends axially from an inflow opening 60 at one end of body 26 to an aperture, or outlet opening, 64, at surface 42 of body 26. Another aperture, or inlet opening, 66 is defined in surface 42 adjacent to aperture 64 so that fluid can flow from aperture 64 to aperture 66, as shown by an arrow 68 in FIG. 1. An outflow conduit, or fluid flow passageway, 70 extends axially from an outlet opening 72 at the outer end of nozzle 28 to aperture 66.

Sleeve 22, rotatably mounted on body 26 and concentric therewith, includes an annular internal closure element, or fluid controller, 46 and an outer operator portion 48. Closure element 46 is made of an elastomeric material and is dimensioned so that its inner surface 46a fits in sealing engagement about surface 42 of body 26. An annular end 46b of the closure element having a rounded cross-sectional configuration sealingly abuts a flat annular abutment side 38 of head portion 34 which extends outwardly from cylindrical sidewall 42. The sleeve is held in place by a snap-ring 52 received in groove 44 of body 26, a protective spacer ring 54, and a sealing O-ring 56 which sealingly engages surface 42. Operator portion 48 has a knurled, or corrugated, outer gripping surface 50 to permit manual rotation of sleeve 22 about body 26.

The rounded end 46b of closure element 46 is specifically designed to provide an effective seal between the closure element and abutment side 38 of head portion 34 when the parts are assembled as illustrated. Integral end 46b functions in much the same manner as an elastomeric O-ring would to press tightly against side 38 and conform as needed to produce a fluid-tight seal.

O-ring 56, closure element 46, and body surface 42 define therebetween a fluid flow chamber, or passage, 65. As is shown by arrow 68 in FIG. 1, when openings 64, 66 of conduits 58, 70 are not occluded by closure element 46 fluid may flow freely via passage 65 from one to the other.

Figure 4:
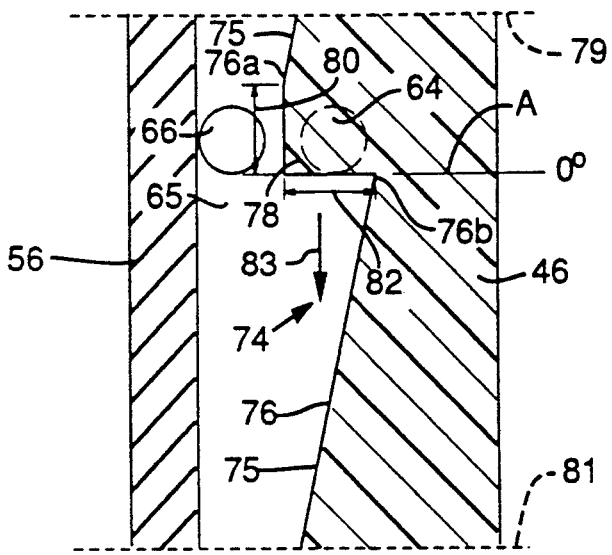
FIG. 4 is an enlarged view of a cylindrical body surface in the assembly with conduit openings and an overlying annular rotatable flow control sleeve with a helical closure element, all of which have been extended to planar orientations for illustrative purposes.
Figure 5:
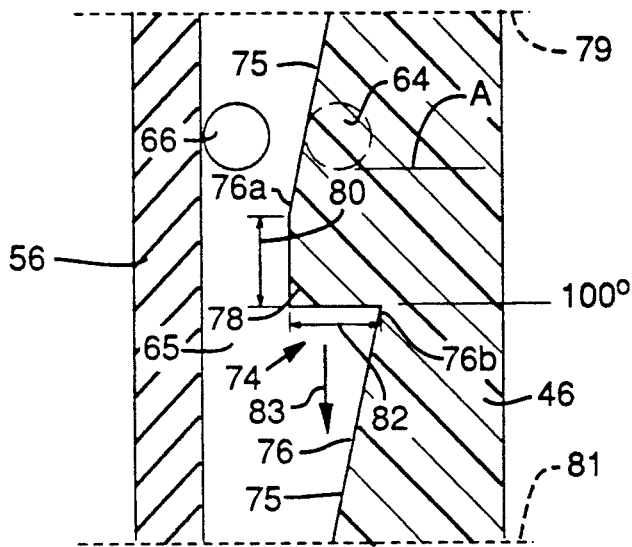
FIG. 5 is a view similar to FIG. 4, but with the closure element rotated to a different position.
Figure 6:
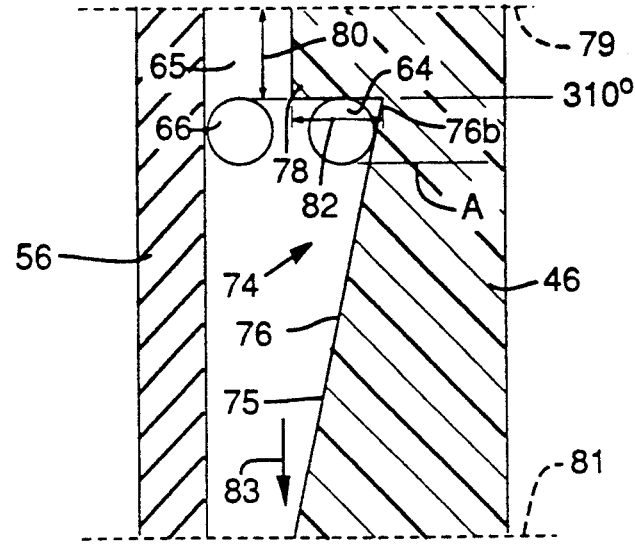
FIG. 6 is a view similar to FIG. 4, but with the closure element rotated to a position to expose both conduit openings.

A helical groove 74, is defined by a helical wall 75 on closure element 46. In FIGS. 4–6, a view has been taken somewhat along line 4—4 in FIG. 1. However, closure element 46, surface 42, and O-ring 56 are illustrated as if extended into planar elements to simplify illustration of the operation of this structure. In their actual cylindrical configurations, dotted lines 79 and 81 are parallel and contiguous.

Wall 75 has a gradually sloping helical first surface 76 and a shelf portion 78 comprising a straight wall section of length 80 and width 82 extending between opposite ends 76a, 76b of wall surface 76. Sleeve 22 and element 46 are mounted for complete and continuous rotation in either direction about surface 42 of body 26 as shown in FIGS. 4–6. Length 80 of shelf 78 is equivalent to a rotation of about 60° of the sleeve, and the length of helical surface 76 is equivalent to a rotation of 300°.

Conduit outlet 64, as shown in FIG. 4, is completely occluded by shelf 78 of closure element 46 when sleeve 22 is positioned at what is defined as a 0° position relative to a line A at an edge of opening 64. By rotating sleeve 22 about 100° in a first direction (i.e., causing shelf 78 to move from 0° in FIG. 4 to about 100° in FIG. 5 in the direction of arrow 83) opening 64 is still completely occluded by the closure element, thus preventing flow of fluid through chamber 65. Continued rotation of sleeve 22 beyond 100° gradually opens outlet 64. At 310°, as illustrated in FIG. 6, opening 64 is fully opened and fluid can flow freely between opening 64 and opening 66. Rotation of the sleeve thus produces selected changes in the dimensions of the fluid flow passage between openings 64 and 66.

Further rotation in the direction of arrow 83 from 310° to about 360° (or 0° as shown in FIG. 4) rapidly reduces the flow through valve assembly 20. This rapid reduction in flow is because shelf 78 occludes inflow opening 64 much quicker than sloping surface 76.

Explaining further, when sleeve 22 is at the 310° position as shown in FIG. 6, opening 64 can be completely occluded rather quickly by turning sleeve 22 about 50° further in the direction of arrow 83 to return to the 0° position (as shown in FIG. 4), or it may be occluded more gradually by turning sleeve 22 approximately 210° in the opposite direction to the 100° position (as shown in FIG. 5).

Figure 7:
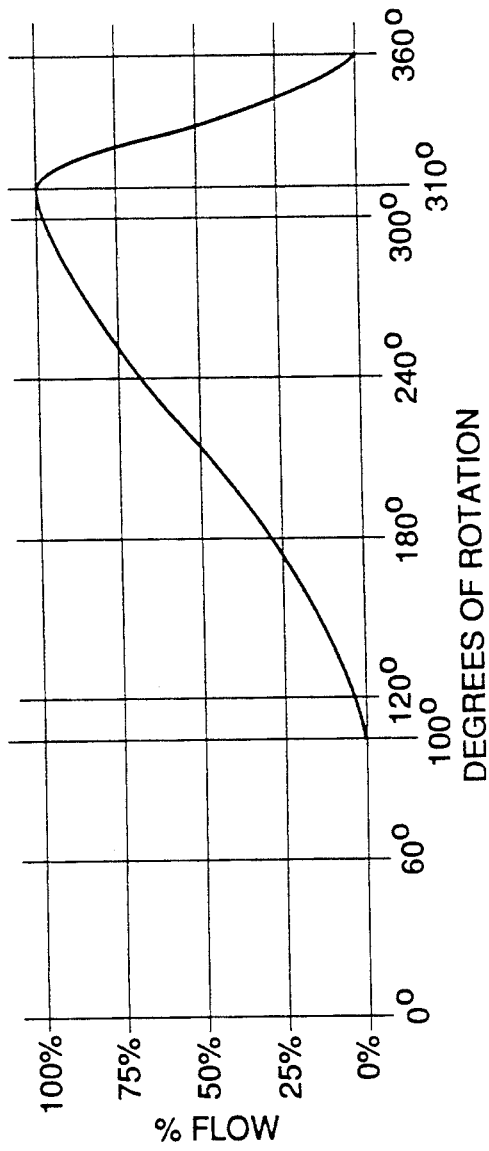
FIG. 7 is a chart illustrating variations in fluid flow rate in the fluid path as the flow control sleeve is rotated.

The flow rate permitted through the valve assembly at different degrees of rotation of sleeve 22 are graphically illustrated in FIG. 7. It will be seen that between 0° and 100° of rotation from the position illustrated in FIG. 4 no flow occurs. Progressive rotation from 100° to 310° produces gradual flow increase from 0% to 100% flow. Further rotation from 310° to 360° produces rapid decrease (shut-off) of fluid flow.

In operation, the fluid flow in the bores through valve assembly 20 is controlled by rotation of sleeve 22. When sleeve 22 is rotated into the shutoff position (0°–100°), all flow of fluid through valve assembly 20 is stopped because outlet 64 of bore 58 is completely occluded by shelf 78 of closure element 46. Rotation of sleeve 22 away from the shutoff position gradually opens a fluid path through the valve, thereby permitting fluid to flow to outflow bore 70 and into a tube 23 attached to nozzle 28. As a result, the rate of fluid flow through valve assembly 20 is increased or decreased by selected rotation of sleeve 22.

In the illustrated embodiment, opening 66 remains open regardless of the position of closure element 46. However, it is contemplated to design sleeve 22 so that the closure element also could cover opening 66 when sleeve 22 is rotated into a shutoff position.

Figure 8:
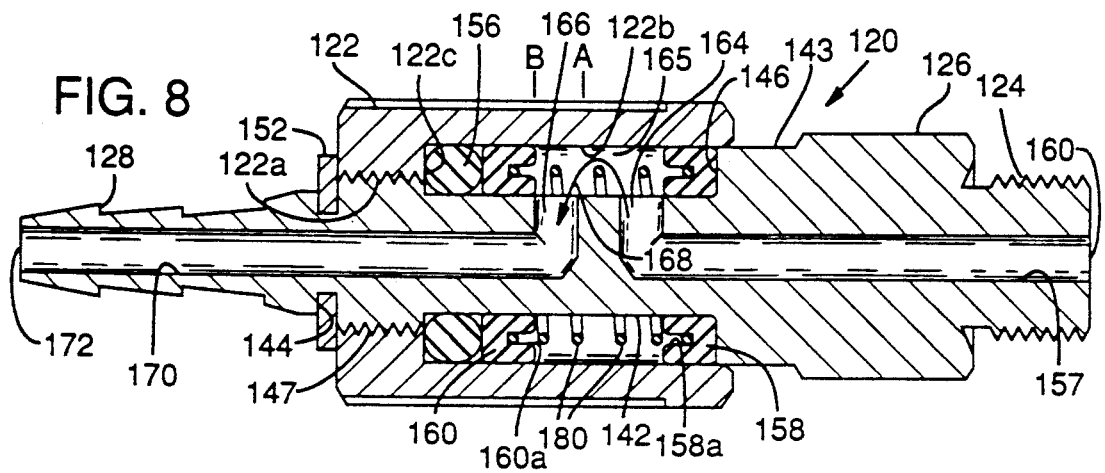
FIG. 8 is a cross-sectional view of a valve assembly according to another embodiment of the invention in an open-flow position.
Figure 9:
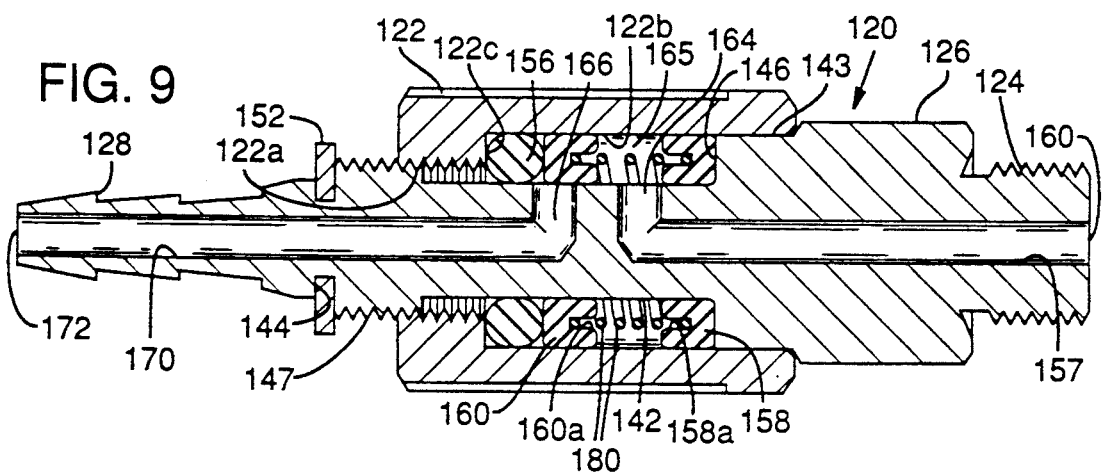
FIG. 9 is a view similar to FIG. 8 with the valve assembly in a shutoff position.

Referring now to FIGS. 8 and 9, a valve assembly 120 according to another embodiment of the invention is illustrated for controlling fluid flow therethrough. The flow of fluids is controlled by rotation and axial shifting of a cylindrical flow control sleeve 122, also referred to herein as a housing. Sleeve 122 is illustrated in FIG. 8 in its open position allowing fluid to flow through the valve, and in FIG. 9 is illustrated in its fully closed, or shutoff, position.

Valve assembly 120 comprises an elongate, generally cylindrical body 126. A cylindrical threaded portion 124 extends from one end thereof. An elongate cylindrical barbed tube connector nozzle 128 extends from the opposite end of body 126. Portion 124 is adapted to be screwed into a threaded socket for receiving fluid and connector nozzle 128 is adapted to receive a flexible tube into which fluid may be dispensed.

Body 126 has a first smooth cylindrical external surface, or sidewall, 142, and a second smooth cylindrical surface of greater diameter 143. An upstanding annular wall 146 extends between surfaces 142, 143. Adjacent the opposite end of surface 142 is an externally threaded section 147. An annular groove 144 is defined between nozzle 128 and threaded section 147.

Sleeve 122 has an internally threaded portion 122a which threadedly engages section 147 on the body. The sleeve also has a substantially smooth cylindrical inner surface 122b sized to slide over the cylindrical outer surface 143 of body 126. An upright annular wall 122c extends between threaded portion 122a and surface 122b.

Sleeve 122 may be gripped by the user and rotated about its longitudinal axis to screw it along threaded portion 147 from the open position illustrated in FIG. 8, to the shutoff, or closed, position illustrated in FIG. 9. A snap ring 152 received in groove 144 serves to limit the movement of sleeve 122 toward its open position and keep it from being screwed off the body until the ring is physically removed.

An internal inflow conduit, or fluid flow passageway, 157 extends axially from an inflow opening 160 to an aperture, or outlet opening, 164 at surface 142 of body 126. Another aperture, or inlet opening, 166 is defined at surface 142 adjacent aperture 164. An annular fluid flow chamber, or passage, 165 is defined between sleeve 122 and surface 142 of the body so that fluid can flow from aperture 164 to aperture 166 as shown by arrow 168 in FIG. 8. An outflow conduit, or fluid flow passageway, 170 extends axially from an outlet opening 172 at the outer end of nozzle 128 to aperture 166.

Mounted within sleeve 122 are an O-ring seal 156, an annular seating element 158, and an annular closure element 160. The O-ring seal is made of an elastomeric material and is of such size as to fit tightly and provide a seal between surfaces 142, 122b and against wall 122c of the sleeve.

Seating element 158 also is made of an elastomeric material with a substantially U-shaped cross-sectional configuration. It fits rather tightly between surfaces 142, 122b and against wall 146, to provide a seal between the sliding sleeve 122 and portion 143 of the main valve body.

Annular closure element 160 also is made of an elastomeric material. It has a substantially U-shaped cross-section, similar to seating element 158, rests tightly against O-ring 156, and is sealingly engaged between surfaces 142, 122b of the body and sleeve.

Seating element 158 and closure element 160 each have annular grooves 158a, 160a, respectively, defined in their facing surfaces adapted to receive opposite ends of a coil spring, or biasing element, 180. The coil spring is of such length that it is constantly in compression between elements 158, 160 from the open position illustrated in FIG. 8 to the closed position illustrated in FIG. 9, and constantly urging them apart. This serves to hold closure element 160 tightly against O-ring 156 as the sleeve is moved between the open and closed positions.

As is seen in FIG. 8, when the sleeve is screwed to its full open position against snap ring 152, apertures 164, 166 are unimpeded and fluid may flow freely from one to the other. As sleeve 122 is rotated about the longitudinal axis of the body, it will move gradually from the open position shown in FIG. 8 to the closed position illustrated in FIG. 9. As this occurs aperture 166 is gradually occluded by closure element 160 until it is fully shutoff as illustrated in FIG. 9.

The screw threads are such that it will require several turns of the sleeve to move from full open to full closed positions. With such construction greater sensitivity in flow rate control may be achieved.

Figure 10:
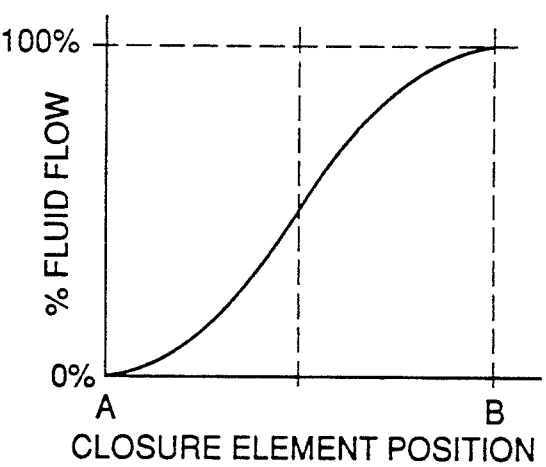
FIG. 10 is a chart illustrating variations in fluid flow rate as the valve is shifted from its shutoff to its open position.

The flow rate permitted through the valve assembly at different positions of the sleeve relative to the body are graphically illustrated in FIG. 10. It will be seen that on moving from the fully closed position, noted as position "A" in FIG. 8, to the fully open position, noted as position "B", a rather smooth transition and graduation in fluid flow may be obtained as the user screws the sleeve along the housing.

While the present invention has been described in accordance with a preferred embodiment, it is to be understood that certain substitutions and alterations may be made thereto without departing from the spirit and scope of the following claims.

We claim:

1. A fluid flow controlling valve assembly comprising:
   a body including a first conduit having an aperture opening to a surface of said body, and a second conduit having an aperture opening to a surface of said body; and
   a sleeve mounted on the body forming a chamber therebetween defining a fluid flow passage between said first conduit and said second conduit, the sleeve being rotatable around the body and operable to change the dimension of the fluid flow passage to control fluid flow between said first and second conduits, said sleeve including a variable cross-section closure element therein having a helical configuration extending about a major portion of the closure element operable upon rotation of the sleeve to a first position to open said fluid flow passage and upon rotation of the sleeve to a second position to restrict such fluid flow passage.

2. The valve assembly of claim 1, wherein the closure element is positioned to occlude a conduit when the sleeve is rotated to said second position for inhibiting fluid flow, is positioned to open said conduit when the sleeve is rotated to said first position to permit fluid flow, and the configuration of the closure element is such that rotation of the sleeve to intermediate positions between said first and second positions varies the amount of fluid flow in graduations dependent upon the degree of rotation of the sleeve.

3. The valve assembly of claim 1, wherein said portion of the closure element having a helical configuration has a variable cross-section which changes gradually on progressing in one direction of rotation of the sleeve to produce a first graduated opening of the fluid flow passage and the closure element has a second portion of more rapid change in cross-section on progressing in the opposite direction of rotation of the sleeve to produce a more rapid opening of the passage then occurs on rotation in said one direction.

4. A valve assembly comprising:
   a body having a first conduit defined therein having an outlet opening in a selected region of the surface of the body and a second conduit having an inlet opening at a second selected region of the surface of the body;
   a sleeve mounted in sealing engagement and for rotation on said body defining a chamber into which both said inlet and outlet openings extend, said chamber providing a fluid flow passage between said inlet and outlet openings, and an adjustable fluid controller mounted within said chamber shiftable between selected positions to vary the fluid flow passage between the outlet and the inlet openings of said conduits, said controller including a closure element having a substantially helical configuration extending about a major portion of the closure element operable on rotation of the sleeve to selectably occlude one of the conduit openings at the surface of the body to selectively open and close the opening of the conduit on said body.

5. A valve assembly connectable to a fluid source comprising
an elongate body having a first end and a second end;
a first fluid flow passageway in said body having an inlet and an outlet;
a second fluid flow passageway in said body having an inlet and an outlet, the inlet of the second passageway being positioned adjacent to the outlet of the first passageway, and
valve means mounted on the body and configured for defining a fluid flow path from the outlet of the first passageway to the inlet of the second passageway and for regulating the flow of fluid therebetween, said valve means comprising a sleeve mounted in sealing engagement on and rotatable about said body, and having an internal bore with a helical groove extending about a major portion of the sleeve configured and positioned on said sleeve to gradually occlude the outlet of the first passageway as the sleeve is rotated in one direction.

6. The valve assembly of claim 5, wherein the valve means comprises a sleeve mounted in sealing engagement on and rotatable about said body, said sleeve having an internal bore with a helical groove.

7. The valve assembly of claim 5, wherein the body includes a sidewall, and the outlet of the first passageway and the inlet of the second passageway extend through the sidewall.

8. The valve assembly of claim 5, wherein the inlet of the first passageway extends through a first end of the body, and the outlet of the second passageway extends through the opposite end of the body.

9. The valve assembly of claim 5, wherein said body has a substantially cylindrical sidewall, the outlet of the first passageway and the inlet of the second passageway extend through said cylindrical sidewall, and said sleeve is mounted for rotation on said cylindrical sidewall.

10. The valve assembly of claim 9, wherein said body further comprises an annular abutment side extending outwardly from said cylindrical sidewall, and said sleeve is constructed of an elastomeric material and has an annular end with a rounded cross sectional configuration sealingly engaging said abutment side.

11. A fluid flow controlling valve assembly comprising:
a body including a first conduit having an aperture opening to a surface of said body, and a second conduit having an aperture opening to a surface of said body; and
a sleeve mounted on the body forming a chamber therebetween defining a fluid flow passage between said first conduit and said second conduit, and a closure element in said sleeve, the sleeve and closure element being movable relative to the body and operable to change the dimension of the fluid flow passage to control fluid flow between said first and second conduits, said body and sleeve having mating helical threaded sections whereby said sleeve is threadably connected to the body for rotation thereabout and upon rotation about the body the sleeve and its associated closure element are shiftable longitudinally of the body between longitudinally spaced first and second positions, wherein the closure element is positioned to occlude one of said conduits when the sleeve is moved to said second position and is positioned to open said one conduit when the sleeve is moved to said first position.

12. The valve assembly of claim 11, wherein the threaded connection between the body and sleeve is such that rotation of the sleeve varies the amount of fluid flow in graduations dependent upon the amount of rotation of the sleeve.

13. The valve assembly of claim 11, wherein said chamber is an annular opening defined between the body and sleeve, and the closure element comprises an annular element sealingly interposed between said sleeve and body in said chamber which element is shiftable with said sleeve between said first and second positions.

14. A fluid flow controlling valve assembly comprising:
a body including a first conduit having an aperture opening to a surface of said body; and a second conduit having an aperture opening to a surface of said body;
a sleeve mounted on the body with an annular opening therebetween forming a chamber defining a fluid flow passage between said first conduit and said second conduit, and a closure element in said sleeve comprising an annular element sealingly interposed between the sleeve and body in said chamber, the sleeve and closure element being movable relative to the body and operable to change the dimension of the fluid flow passage to control fluid flow between said first and second conduits, said sleeve being threadably connected to the body for rotation thereabout and upon rotation about the body the sleeve and its associated closure element being shiftable longitudinally of the body between first and second positions, wherein the closure element is positioned to occlude one of said conduits when the sleeve is moved to said second position and is positioned to open said one conduit when the sleeve is moved to said first position; and
a biasing element operatively urging said closure element toward one of its positions and said sleeve is operable to move the closure element against the urging of said element toward its other position upon rotation of the sleeve.

15. The valve assembly of claim 14, wherein said biasing element comprises a compression spring.

16. The valve assembly of claim 14, wherein said sleeve has a skirt portion mounted to move over an outer surface of the body, and a sealing member is interposed between said skirt portion and outer surface to provide a fluid-tight seal therebetween.

* * * * *